US010828325B2

(12) United States Patent
Richards

(10) Patent No.: US 10,828,325 B2
(45) Date of Patent: Nov. 10, 2020

(54) HYPOCHLORITE COMPOSITIONS FOR THE TREATMENT OF TRAUMATIC BRAIN INJURY

(71) Applicant: Reoxcyn, LLC, Pleasant Grove, UT (US)

(72) Inventor: Kurt Richards, Herriman, UT (US)

(73) Assignee: REOXCYN, LLC, Pleasant Grove, UT (US)

( * ) Notice: Subject to any disclaimer, the term of this patent is extended or adjusted under 35 U.S.C. 154(b) by 21 days.

(21) Appl. No.: 16/211,705

(22) Filed: Dec. 6, 2018

(65) Prior Publication Data

US 2019/0192557 A1    Jun. 27, 2019

Related U.S. Application Data

(60) Provisional application No. 62/609,810, filed on Dec. 22, 2017.

(51) Int. Cl.
| | |
|---|---|
| *A61K 33/20* | (2006.01) |
| *A61P 25/28* | (2006.01) |
| *A61K 47/24* | (2006.01) |
| *A61K 47/02* | (2006.01) |
| *A61P 25/00* | (2006.01) |
| *A61K 9/08* | (2006.01) |

(52) U.S. Cl.
CPC ............... *A61K 33/20* (2013.01); *A61K 9/08* (2013.01); *A61K 47/02* (2013.01); *A61K 47/24* (2013.01); *A61P 25/00* (2018.01); *A61P 25/28* (2018.01)

(58) Field of Classification Search
None
See application file for complete search history.

(56) References Cited

U.S. PATENT DOCUMENTS 9,474,768 B1 * 10/2016 Richards ............... A61P 31/18
2012/0039958 A1 * 2/2012 Watson ............... A61K 31/137
424/400
2016/0317577 A1 * 11/2016 Hoover ............... A61K 47/32

* cited by examiner

*Primary Examiner* — Jessica Worsham
(74) *Attorney, Agent, or Firm* — Knobbe, Martens, Olson & Bear LLP

(57) ABSTRACT

Described herein are compositions that include hypochlorite and methods of alleviating, ameliorating, palliating, reducing, or treating a traumatic brain injury or neurological disorder, such as a concussion, with such composition. The composition may further include a salt, a buffer, a rheology agent, or a silicone polymer or blend thereof. The salt may include halite, table salt, common salt, curing salt, flake salt, Epsom salt, sea salt, Alaea salt (or Hawaiian sea salt), Alpenbergkern salt, Anglesey Sea salt, Dead Sea salt, Himalayan sea salt, Kalahari salt, Maras salt, Murray River salt flakes, Namibian salt pearls, Persian blue fine salt, Polish mine salt, primordial sea salts, Sal de Tavira, Sale Marino di Trapani, Sel de Guérande, South African Sea salt, Utah salt, black lava salt, brine, rock salt, red rock salt, or kosher salt, or combinations thereof.

18 Claims, No Drawings

HYPOCHLORITE COMPOSITIONS FOR THE TREATMENT OF TRAUMATIC BRAIN INJURY

RELATED APPLICATIONS

This application claims the benefit of priority to U.S. Provisional Patent Application No. 62/609,810, filed Dec. 22, 2017, the disclosure of which is incorporated by reference herein in its entirety.

FIELD

The present disclosure relates to methods and compositions for alleviating, ameliorating, palliating, reducing, or treating traumatic brain injuries or other neurological disorders in a subject. More particularly, the present disclosure relates to a composition including hypochlorite formulated for alleviating, ameliorating, palliating, or treating traumatic brain injuries, such as a concussion.

BACKGROUND

In the United States, at least 2.8 million people sustain a traumatic brain injury (TBI) each year. Injuries to the brain result in a variety of outcomes, including more than 50,000 deaths and more than 280,000 hospitalizations annually. The leading causes of TBI include falls and being struck by or against an object.

Mild TBIs, such as concussion, include trauma that can cause long term injury to the brain. Cumulative concussions increase the likelihood of permanent neurological disability. Concussions are one of the commonest forms of TBI. A concussion can be defined as a complex pathophysiological process affecting the brain, induced by traumatic biomechanical forces. Concussions may result in a variety of symptoms, including headache, dizziness, nausea, physical impairment (for example, unsteadiness), cognitive impairment (for example, confusion or memory loss), blurred vision, and abnormal behavior. Traditionally, concussions have been treated through physical and cognitive rest. TBIs such as concussions are complex and involve a variety of signs and symptoms that vary from patient to patient. While the identification of concussions has improved in recent years, there remains a need for improved treatment.

SUMMARY

It is therefore an aspect of this disclosure to provide compositions and method of use thereof for the alleviation, amelioration, palliation, reduction, or treatment of traumatic brain injuries or other neurological disorders in a subject, such as a concussion.

Some embodiments provided herein related to a method of treating a traumatic brain injury (TBI) in a subject. In some embodiments, the TBI is a concussion. In some embodiments, the method includes administering to a subject a composition comprising hypochlorite. In some embodiments, the composition further includes a salt, a buffer, a rheology agent, and a silicone polymer or blend thereof.

In some embodiments, the salt includes halite, table salt, common salt, curing salt, flake salt, Epsom salt, sea salt, Alaea salt (or Hawaiian sea salt), Alpenbergkern salt, Anglesey Sea salt, Celtic sea salt, Dead Sea salt, Himalayan sea salt (including Himalayan pink sea salt), Kalahari salt, Maras salt, Murray River salt flakes, Namibian salt pearls, Persian blue fine salt, Polish mine salt, primordial sea salts, Sal de Tavira, Sale Marino di Trapani, Sel de Guérande, South African Sea salt, Utah salt, black lava salt, brine, rock salt, red rock salt, fleur de sel, or kosher salt, or combinations thereof. In some embodiments, the salt is present in an amount of 0.01% to about 0.1% w/v.

In some embodiments, the buffer includes sodium phosphate monobasic. In some embodiments, the buffer is present in an amount of about 0.5% to about 5% w/v. In some embodiments, the rheology agent includes sodium magnesium silicate. In some embodiments, the rheology agent is present in an amount of about 0.5% to about 10% w/v. In some embodiments, the silicone polymer or blend thereof includes dimethicone. In some embodiments, the silicone polymer or blend thereof is present in an amount of about 0.5% to about 10% w/v.

In some embodiments, the composition is formulated as a pharmaceutically acceptable dosage form. In some embodiments, the composition is administered by nasal, oral, parenteral, pulmonary, rectal, sublingual, topical, or vaginal administration. In some embodiments, the composition is formulated as an aerosol, a balm, a bead, a caplet, a capsule, a cream, a dragee, a drop, an emollient, a foam, a gel, a granule, a gummy, an inhalable, an injectable, a liquid, a lotion, a lozenge, a meltable solid, a mist, an ointment, a paste, a patch, a pellet, a pill, a powder, a slurry, a soft gel, a solution, a sponge, a spray, a spritz, a strip, a suppository, a suspension, a syrup, a tablet, a tape, or a vapor. In some embodiments, the composition is administered to the subject at least twice daily. In some embodiments, administration of the composition reduces symptoms of a TBI.

DETAILED DESCRIPTION

Embodiments provided herein relate to methods and compositions for the alleviation, amelioration, palliation, reduction, or treatment of traumatic brain injuries or other neurological disorders in a subject, such as a concussion. The methods of alleviating, ameliorating, palliating, reducing, or treating a traumatic brain injury (TBI), including a concussion, include administering to a subject or patient having a TBI such as a concussion, a composition including hypochlorite. Also provided are compositions that include hypochlorite. In certain embodiments, the composition is formulated for administration to a subject, and upon administration, the TBI, such as a concussion, is alleviated, ameliorated, palliated, reduced, or treated. In certain embodiments, administration of the composition alleviates, ameliorates, palliates, reduces, or treats symptoms of a TBI, such as symptoms of a concussion.

It will be readily understood that the aspects of the present disclosure, as generally described herein, can be arranged, substituted, combined, separated, and designed in a wide variety of different configurations, all of which are explicitly contemplated herein.

Unless defined otherwise, technical and scientific terms used herein have the same meaning as commonly understood by one of ordinary skill in the art to which the present disclosure belongs. All patents, applications, published applications and other publications referenced herein are expressly incorporated by reference in their entireties unless stated otherwise. For purposes of the present disclosure, the following terms are defined below.

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length. When a value is preceded by the term about, the component is not intended to be limited strictly to that value, but it is intended to include amounts that vary from the value.

Throughout this specification, unless the context requires otherwise, the words "comprise," "comprises," and "comprising" will be understood to imply the inclusion of a stated step or element or group of steps or elements but not the exclusion of any other step or element or group of steps or elements.

Some embodiments described herein relate to compositions for the alleviation, amelioration, palliation, reduction, or treatment of traumatic brain injuries or other neurological disorders in a subject, such as a concussion. Compositions disclosed herein include hypochlorite.

The terms "composition" or "formulation" as used herein refer to their generally accepted meaning in the art. These terms generally refer to a composition or formulation, such as in a pharmaceutically acceptable carrier or diluent, in a form suitable for administration, for example, systemic or local administration, into a cell or subject, including, for example, a human. Suitable forms, in part, depend upon the use or the route of entry, for example in vitro contact to a cell in isolation or administration to a cell located in situ in a subject by administration via oral, transdermal, inhalation, or by injection. Such forms should not prevent the composition or formulation from reaching a target cell. For example, compositions injected into the blood stream should be soluble. Other factors are known in the art, and include considerations such as toxicity and forms that prevent the composition or formulation from exerting its effect. As used herein, pharmaceutical formulations include formulations for human and veterinary use. A "pharmaceutically acceptable composition" or "pharmaceutically acceptable formulation" can refer to a composition or formulation that allows for the effective distribution of the hypochlorite to the physical location most suitable for treatment of a TBI.

The term "physiologically acceptable" defines a carrier, diluent, or excipient that does not abrogate the biological activity and properties of the compound.

A "pharmaceutically acceptable carrier" refers to a substance, not itself a therapeutic agent, which may facilitate the incorporation of a compound into cells or tissues. The carrier may be a liquid for the dissolution of a compound to be administered by ingestion. The carrier may be a vehicle for delivery of a therapeutic agent to a subject. The carrier may improve the stability, handling, or storage properties of a therapeutic agent. The carrier may facilitate formation of a dose unit of a composition into a discrete article such as a solution, capsule, tablet, film coated tablet, powder caplet, gel cap, pill pellet, suppository, or bead, and the like suitable for nasal, oral, parenteral, pulmonary, rectal, sublingual, topical, or vaginal administration to a subject.

As used herein, a "diluent" refers to an ingredient in a pharmaceutical composition that lacks pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion, or inhalation. A common form of diluent in the art is a buffered aqueous solution such as, without limitation, phosphate buffered saline that is physiologically compatible with human cells and tissues.

As used herein, an "excipient" refers to an inert substance that is added to a pharmaceutical composition to provide, without limitation, bulk, consistency, stability, binding ability, lubrication, or disintegrating ability to the composition.

"Hypochlorous acid" or "hypochlorite" as used herein, refers to a weak acid having the chemical formula HClO. Hypochlorous acid is also known as chloric (I) acid, chloranol, or hydroxidochlorine. Salts of hypochlorite are also referred to herein and can include sodium hypochlorite (NaClO), calcium hypochlorite ($Ca(ClO)_2$), or potassium hypochlorite (KClO). Hypochlorite, or acids and salts thereof, may be used in the compositions of the present disclosure at an amount of about 0.5%, 1%, 5%, 10%, 15%, 20%, 25%, 30%, 40%, 50%, or greater w/v %, or within a range defined by any two of the aforementioned amounts. In some embodiments, the w/v % of hypochlorite or an acid or salt thereof is about 25% w/v. In some embodiments, the hypochlorite salt or hypochlorous acid is added directly to the composition. In some embodiments, the final amount of hypochlorite or an acid or salt thereof is less than, greater than, or equal to about 10, 15, 20, 25, 30, 35, 40, 45, 50, 55, 60, 65, 70, 75, 80, 85, 90, 95, 100, 120, 150, 175, 200, 300 ppm or within a range defined by any two of the aforementioned amounts. In some embodiments, the amount of hypochlorite or an acid or salt thereof in the composition is between about 50 to about 100 ppm. In some embodiments, the amount of hypochlorite or an acid or salt thereof in the composition is about 75 ppm.

As used herein, a "subject" or a "patient" refers to an animal that is the object of treatment, observation, or experiment. "Animal" comprises cold- and warm-blooded vertebrates and invertebrates such as fish, shellfish, reptiles and, in particular, mammals. "Mammal" comprises, without limitation, mice, rats, rabbits, guinea pigs, dogs, cats, sheep, goats, cows, horses, primates, such as monkeys, chimpanzees, and apes, and, in particular, humans. In some alternatives, the subject is human.

Some embodiments disclosed herein relate to selecting a subject or patient in need. In some embodiments, a patient is selected who is in need of treatment of a TBI, such as a concussion. In some embodiments, a patient is selected who is suspected of being at risk for onset of a TBI, such as a concussion. In some embodiments, a patient is selected who is likely to be exposed to conditions resulting in onset of a TBI, such as a concussion. In some embodiments, a patient is selected who has been diagnosed with a TBI, such as a concussion. In some embodiments, a patient is selected who is suspected of having a TBI, such as a concussion. In some embodiments, a patient is selected who has previously been treated for a TBI, such as a concussion. In some embodiments, a patient is selected who has previously been treated for being at risk of a TBI, such as a concussion. In some embodiments, a patient is selected who has developed a recurrence of a TBI, such as a concussion. In some embodiments, a patient is selected who may have any combination of the aforementioned selection criteria.

Some embodiments provided herein relate to alleviating, ameliorating, palliating, reducing, or treating TBIs or other neurological disorders in a subject. In some embodiments, the method includes administering a composition including hypochlorite to a subject having or suspected of having a TBI, such as a concussion.

Traumatic brain injury, or TBI, as used herein refers to an acquired brain injury or a head injury, when a trauma causes damage to the brain. Trauma includes, e.g., post-head trauma, impact trauma, and other traumas to the head such as, for example, traumas caused by accidents and/or sports injuries, concussive injuries, penetrating head wounds, brain tumors, stroke, heart attack, meningitis, viral encephalitis, and other conditions that deprive the brain of oxygen. In some embodiments, the trauma is an external, physical force. The damage can be focal (confined to one area of the brain) or diffuse (involving more than one area of the brain). Clinically, TBI can be rated as mild, moderate, or severe based on TBI variables that include duration of loss of consciousness (LOC), Glasgow Coma Score (GCS), or post-traumatic stress amnesia.

In some embodiments, the TBI can be chronic, where the brain is subject to repeated traumatic injury to the brain. Generally, chronic TBI is typically a mild to moderate form of closed brain injury repeatedly suffered by a subject (e.g., athlete, combat soldier), resulting in increased incidence of impaired motor, cognitive, and/or behavioral impairments months to years following the traumatic brain injuring events. Individuals subjected to such chronic brain injury appear to have increased susceptibility to various neurological disorders, including, for example Alzheimer's disease, Parkinson's disease, and/or chronic traumatic encephalopathy (CTE).

In some embodiments, the TBI can result from a closed head injury. The closed head injury may be transient or prolonged. A "closed head injury" refers to a brain injury when the head suddenly and violently hits an object but the object does not break through the skull. In some embodiments, the closed head injury is a concussion or contusion. A concussion is a mild form of TBI resulting in temporary impairment of neurological function which quickly resolves by itself, and where there are generally no gross structural changes to the brain as the result of the condition. A contusion is a distinct area of swollen brain tissue mixed with blood released from broken blood vessels. A contusion can also occur in response to shaking of the brain back and forth within the confines of the skull, an injury referred to as contrecoup. As used herein, a closed head injury refers to an injury due to an external, physical trauma and does not encompass brain injury resulting from "internal" forces such as ischemia/reperfusion and stroke.

As used herein, "symptom" refers to any subjective evidence of disease or of a patient's condition, and "sign" or "clinical sign" refers to an objective physical finding relating to a particular condition capable of being found by one other than the patient. Symptoms of a TBI, such as a concussion, may include headache, dizziness, vomiting, nausea, physical impairment, weakness or numbness in the limbs, lack of motor coordination, difficulty balancing, convulsions, lightheadedness, lethargy, ringing in the ears, blurred vision, dilation of one or both pupils, slurred speech, aphasia, dysarthria, bad taste in the mouth, changes in sleep patterns, cognitive impairment, confusion, memory loss, abnormal behavior, mood changes, agitation, or difficulty with memory, concentration, attention, or thinking.

As used herein, the term "alleviate," "alleviating," or "alleviation" refers to lessening or making less severe, one or more symptom of a TBI, such as a concussion.

As used herein, the term "ameliorate," "ameliorating," or "amelioration" refers to any reduction in the extent, severity, frequency, and/or likelihood of a symptom or clinical sign characteristic of a TBI, such as a concussion.

As used herein, the term "palliate," "palliating," or "palliation" refers to reducing the subjective experience of symptoms of a TBI, such as a concussion. As used herein, "eliminate" is used to mean the relief of symptoms of a TBI, such as a concussion to the point at which the patient no longer feels an effect of said a TBI. As used herein, "prevent" means prophylactic protection against the occurrence of symptoms of a TBI, such as a concussion. Thus, in some embodiments, a composition is administered to a subject suspected of being at risk for a TBI, such as a concussion, as a prophylactic means of minimizing, reducing, or eliminating the onset of symptoms or physiological responses of a TBI, such as a concussion.

As used herein, the term "reduce," "reducing," or "reduction" refers to the decrease or prevention of an increase in a symptom or underlying cause of a symptom of a TBI, such as a concussion. The reduction can be by 5%, 10%, 20%, 30%, 40%, 50%, 60%, 70%, 80%, 90%, or 100%, or an amount that is within a range defined by any two of the aforementioned values. A partial reduction may be realized.

As used herein, the terms "treating," "treatment," "therapeutic," or "therapy" do not necessarily mean total cure or abolition of the disease or condition. In some embodiments, treatment can include treatment of a symptom of a TBI, such as a concussion, or treatment of an underlying cause of a symptom of a TBI, such as a concussion. A partial treatment may be realized.

In some embodiments, administering the composition including hypochlorite to a subject includes administration by nasal, oral, parenteral, pulmonary, rectal, sublingual, topical, or vaginal routes. The term "therapeutically effective amount" is used to indicate an amount of a composition that is used to alleviate, ameliorate, palliate, reduce, or treat a TBI, such as a concussion, or other neurological disorder in a subject. Determination of a therapeutically effective amount is within the capability of those skilled in the art, in view of the disclosure provided herein. The therapeutically effective amount of the composition disclosed herein required as a dose will depend on the route of administration, the type of animal, including human, receiving administration, the physical characteristics of the specific animal under consideration, the severity and chronicity of the TBI, and the like. The dose can be tailored to achieve a desired effect, but will depend on such factors as weight, diet, concurrent medication and other factors which those skilled in the medical arts will recognize.

In some embodiments, a dose is provided in an amount of about 0.1 ounce to about 12 ounces, such as 0.1, 0.2, 0.3, 0.4, 0.5, 0.6, 0.7, 0.8, 0.9, 1, 2, 3, 4, 5, 6, 7, 8, 9, 10, 11, or 12 ounces, or an amount within a range defined by any two of the aforementioned values. In some embodiments, the dose is administered at a frequency of four times daily to one time monthly, such as 4 times/day, 3 times/day, 2 times/day, 1 time/day, once every other day, 6 times/week, 5 times/week, 4 times/week, 3 times/week, 2 times/week, 1 time/week, once every other week, twice monthly, or once monthly, or an amount within a range defined by any two of the aforementioned frequencies. In some embodiments, the dose is administered for a period of one day to 10 years or more, for example, for a period of one day, one week, one month, six months, one year, two years, three years, four years, five years, six years, seven years, eight years, nine years, ten years, or more, or within a range defined by any two of the aforementioned values.

In some embodiments, the composition is formulated consistent with the mode of administration. For example, the composition may be formulated for nasal administration by preparation of a solution, a spray, a drop, a mist, an aerosol, a powder, a vapor, or a nasal inhalable, or other formulation for nasal administration. The composition may be formulated for oral administration by preparation of a pill, a tablet, a capsule, a caplet, a lozenge, a gummy, a soft gel, a bead, a pellet, a strip, a dragee, a granule, a powder, a slurry, a foam, a drop, a solution, a liquid, a suspension, a syrup, a spray, a mist, a vapor, or an oral inhalable, or other formulation for oral administration. The composition may be formulated for parenteral administration by preparation of an injectable or a solution prepared for intramuscular, subcutaneous, intravenous, and/or intramedullary injection, or other formulation for parenteral administration. The composition may be formulated for pulmonary administration by preparation of an inhalable, a mist, a vapor, or a powder or other formulation for pulmonary administration. The composition may be formulated for rectal administration by preparation of a suppository, a liquid, a solution, or other formulation for rectal administration. The composition may be formulation for sublingual administration by preparation of a tablet, a strip, a drop, a spray, a lozenge, or other formulation for sublingual administration. The composition may be formulated for topical administration by preparation of a paste, a lotion, a gel, a cream, a solution, a liquid, a spray, a spritz, a mist, an ointment, an emollient, a balm, a foam, a patch, a powder, a meltable solid, a sponge, a tape, a vapor, or other formulation for topical administration. The composition may be formulated for vaginal administration by preparation of a tablet, a cream, a suppository, or other formulation for vaginal administration.

Some embodiments provided herein relate to a method of making the composition described herein. Methods of making the composition may include electrolyzing a saline solution having a salt concentration of about 10 g NaCl/gal, such as 10.75 g NaCl/gal using a set of electrodes with an amperage of about 50-60 amps, such as 56 amps to produce an electrolyzed saline solution, wherein the water is chilled below room temperature and the water is circulated during electrolyzing. In some embodiments, the electrolysis is performed sufficient to generate a sufficient amount or concentration of hypochlorite. In some embodiments, electrolysis is performed sufficient to generate an amount of hypochlorite ranging from 1 to 1000 ppm, such as about 1, 2, 3, 4, 5, 6, 7, 8, 9, 10, 15, 20, 25, 30, 35, 40, 45, 50, 55, 60, 65, 70, 75, 80, 85, 90, 95, 100, 120, 150, 175, 200, 300, 400, 500, 600, 700, 800, 900, or 1000 ppm or an amount within a range defined by any two of the aforementioned amounts.

A method of producing the disclosed compositions can include one or more of the steps of (1) preparation of an ultra-pure homogeneous solution of sodium chloride in water, (2) temperature control and flow regulation through a set of inert catalytic electrodes, and (3) a modulated electrolytic process that results in the formation of such stable molecular moieties and complexes. In one embodiment, such a process includes all these steps.

The saline generally should be free from contaminants, both organic and inorganic, and homogeneous down to the molecular level. In particular, metal ions can interfere with the electro-catalytic surface reactions, and thus it may be helpful for metals to be avoided. In one embodiment, a brine solution is used to salinate the water. The brine solution can have a NaCl concentration of about 540 g NaCl/gal, such as 537.5 g NaCl/gal. In one embodiment, the composition can include at least one species such as $O_2$, $H_2$, $Cl_2$, $OCl^-$, $HOCl$, $NaOCl$, $HClO_2$, $ClO_2$, $HClO_3$, $HClO_4$, $H_2O_2$, $Na^+$, $Cl^-$, $H^+$, $H^-$, $OH^-$, $O_3$, $O_4^{*-}$, $^1O$, $OH^{*-}$, $HOCl-O_2^{*-}$, $HOCl-O_3$, $O_2^{*-}$, $HO_2^*$, NaCl, HCl, NaOH, water clusters, or a combination thereof.

In one embodiment, the composition can include at least one species such as $H_2$, $Cl_2$, $OCl^-$, $HOCl$, $NaOCl$, $HClO_2$, $ClO_2$, $HClO_3$, $HClO_4$, $H_2O_2$, $O_3$, $O_4^{*-}$, $^1O_2$, $OH^{*-}$, $HOCl-O_2^{*-}$, $HOCl-O_3$, $O_2^{*-}$, $HO_2^*$, water clusters, or a combination thereof.

In one embodiment, the composition can include at least one species such as $HClO_3$, $HClO_4$, $H_2O_2$, $O_3$, $O_4^{*-}$, $^1O_2$, $OH^{*-}$, $HOCl-O_2^{*-}$, $HOCl-O_3$, $O_2^{*-}$, $HO_2^*$, water clusters, or a combination thereof. In one embodiment, the composition can include at least $O_2^{*-}$ and HOCl.

In one embodiment, the composition can include $O_2$. In one embodiment, the composition can include $H_2$. In one embodiment, the composition can include $Cl_2$. In one embodiment, the composition can include $OCl^-$. In one embodiment, the composition can include HOCl. In one embodiment, the composition can include NaOCl. In one embodiment, the composition can include $HClO_2$. In one embodiment, the composition can include $ClO_2$. In one embodiment, the composition can include $HClO_3$. In one embodiment, the composition can include $HClO_4$. In one embodiment, the composition can include $H_2O_2$. In one embodiment, the composition can include $Na^+$. In one embodiment, the composition can include $Cl^-$. In one embodiment, the composition can include $H^+$. In one embodiment, the composition can include $H^-$. In one embodiment, the composition can include $OH^-$. In one embodiment, the composition can include $O_3$. In one embodiment, the composition can include $O_4^{*-}$. In one embodiment, the composition can include $^1O_2$. In one embodiment, the composition can include $OH^{*-}$. In one embodiment, the composition can include $HOCl-O_2^*$. In one embodiment, the composition can include $HOCl-O_3$. In one embodiment, the composition can include $O_2^{*-}$. In one embodiment, the composition can include $HO_2^*$. In one embodiment, the composition can include NaCl. In one embodiment, the composition can include HCl. In one embodiment, the composition can include NaOH. In one embodiment, the composition can include water clusters. Embodiments can include combinations thereof.

In one embodiment, the method of making a formulation as described herein can include reverse osmosis. As used herein, the term "reverse osmosis" refers to a process of extracting water through a semi-permeable membrane from feed water by applying on the feed water a pressure that is higher than the osmotic pressure of the feed water. Water can be supplied from a variety of sources, including but not limited to municipal water, filtered water, distilled water, nanopure water, or the like.

The reverse osmosis process can vary, but can include providing water having a total dissolved solid content of less than about 10 ppm, such as about 9 ppm, about 8 ppm, about 7 ppm, about 6 ppm, about 5 ppm, about 4 ppm, about 3 ppm, about 2 ppm, about 1 ppm or less.

The reverse osmosis process can be performed at a temperature of about 5° C., about 10° C., about 15° C., about 20° C., about 25° C., about 30° C., about 35° C., or a temperature within a range defined by any two of the aforementioned values. The reverse osmosis step can be repeated as needed to achieve a particular total dissolved solids level. In some embodiments, a distillation step can also be performed, prior to, after, or concomitant with the reverse osmosis step. Distillation as used herein refers to a process boiling water and condensing steam into a separate container to obtain distilled water. Distilled water includes water that is purified to remove minerals such as calcium and magnesium, trace elements, or other impurities by distillation.

Other means of reducing contaminants include filtration and/or purification such as by utilizing deionization, carbon filtration, double-distillation, electrodeionization, resin filtration such as with Milli-Q purification, microfiltration, ultrafiltration, ultraviolet oxidation, electrodialysis, or combinations thereof.

The distillation process can vary, but can provide water having a total dissolved solid content of less than about 5 ppm, about 4 ppm, about 3 ppm, about 2 ppm, about 1 ppm, about 0.9 ppm, about 0.8 ppm, about 0.7 ppm, about 0.6 ppm, about 0.5 ppm, about 0.4 ppm, about 0.3 ppm, about 0.2 ppm, about 0.1 ppm, or less, or an amount within a range defined by any two of the aforementioned values. The temperature of the distillation process can be performed at a temperature of about 5° C., about 10° C., about 15° C., about 20° C., about 25° C., about 30° C., about 35° C., or a temperature within a range defined by any two of the aforementioned values.

The distillation step can be repeated as needed to achieve a particular total dissolved solids level. After water has been subjected to reverse osmosis, distillation, both, or neither, the level of total dissolved solids in the water can be less than about 5 ppm, about 4 ppm, about 3 ppm, about 2 ppm, about 1 ppm, about 0.9 ppm, about 0.8 ppm, about 0.7 ppm, about 0.6 ppm, about 0.5 ppm, about 0.4 ppm, about 0.3 ppm, about 0.2 ppm, about 0.1 ppm, or less, or an amount within a range defined by any two of the aforementioned values.

The reverse osmosis, distillation, both, or neither, can be preceded by a carbon filtration step. Purified water can be used directly with the systems and methods described herein.

In one embodiment, contaminants can be removed from a commercial source of water by the following procedure: water flows through an activated carbon filter to remove the aromatic and volatile contaminants and then undergoes reverse osmosis (RO) filtration to remove dissolved solids and most organic and inorganic contaminants. The resulting filtered RO water can contain less than about 8 ppm of dissolved solids. Most of the remaining contaminants can be removed through a distillation process, resulting in dissolved solid measurements less than 1 ppm. In addition to removing contaminants, distillation may also serve to condition the water with the correct structure and oxidation reduction potential (ORP) to facilitate the oxidative and reductive reaction potentials on the platinum electrodes in the subsequent electro-catalytic process.

After water has been subjected to reverse osmosis, distillation, both or neither, a salt can be added to the water in a salting step. The salt can be unrefined, refined, caked, de-caked, or the like. In some embodiments, the salt is halite, table salt, common salt, curing salt, flake salt, Epsom salt, sea salt, Alaea salt (or Hawaiian sea salt), Alpenbergkern salt, Anglesey Sea salt, Celtic sea salt, Dead Sea salt, Himalayan sea salt (including Himalayan pink sea salt), Kalahari salt, Maras salt, Murray River salt flakes, Namibian salt pearls, Persian blue fine salt, Polish mine salt, primordial sea salts, Sal de Tavira, Sale Marino di Trapani, Sel de Guérande, South African Sea salt, Utah salt, black lava salt, brine, rock salt, red rock salt, fleur de sel, or kosher salt. The salt present in the composition can include a number of elements, including actinium, aluminum, antimony, arsenic, astatine, barium, beryllium, bismuth, boron, bromine, cadmium, calcium, carbon, cerium, cesium, chlorine, chromium, cobalt, copper, dysprosium, erbium, europium, francium, fluorine, gadolinium, gallium, germanium, gold, hafnium, holmium, hydrogen, iodine, indium, iridium, iron, lanthanum, lead, lithium, lutetium, magnesium, manganese, mercury, molybdenum, neptunium, neodymium, nickel, niobium, nitrogen, osmium, oxygen, palladium, phosphorus, platinum, plutonium, polonium, potassium, praseodymium, promethium, protactinium, radium, rhenium, rhodium, rubidium, ruthenium, samarium, scandium, selenium, silicon, silver, sodium, strontium, sulfur, tantalum, technetium, tellurium, terbium, thallium, thorium, thulium, tin, titanium, uranium, vanadium, ytterbium, zinc, or zirconium. In some embodiments, the element present in the salt can be present in an amount of less than 0.001 ppm to an amount of greater than 400,000 ppm.

In some embodiments, the salt may include aluminum in an amount of 114.8 ppm, antimony in an amount of 0.022 ppm, arsenic in an amount of 0.066 ppm, barium in an amount of 0.664 ppm, beryllium in an amount of 0.051 ppm, bismuth in an amount of 0.005 ppm, bromine in an amount of 56.006 ppm, cadmium in an amount of 0.017 ppm, calcium in an amount of 2101 ppm, chromium in an amount of 0.207 ppm, cobalt in an amount of 0.033 ppm, copper in an amount of 0.116 ppm, germanium in an amount of 0.072 ppm, iodide in an amount of less than 0.001 ppm, iron in an amount of 81.722 ppm, lead in an amount of 0.093 ppm, magnesium in an amount of 1944 ppm, manganese in an amount of 1.911 ppm, mercury in an amount of 0.016 ppm, molybdenum in an amount of 0.011 ppm, nickel in an amount of 0.096 ppm, phosphorus in an amount of 5.125 ppm, potassium in an amount of 1728 ppm, selenium in an amount of 0.269 ppm, silver in an amount of 0.004 ppm, sodium in an amount of 388690 ppm, strontium in an amount of 32.223 ppm, tin in an amount of 0.169 ppm, or zinc in an amount of 1.261 ppm or any combination thereof. In some embodiments, the salt may include one or more of the above elements present in 1, 2, 3, 4, 5, 6, 7, 8, 9, or 10% higher or lower than the above-listed amounts.

In some embodiments, the salt may include aluminum in an amount of 0.747 ppm, antimony in an amount of 0.014 ppm, arsenic in an amount of 0.039 ppm, barium in an amount of 0.012 ppm, beryllium in an amount of 0.038 ppm, bismuth in an amount of 0.005 ppm, bromine in an amount of 81.414 ppm, cadmium in an amount of 0.007 ppm, calcium in an amount of 10.625 ppm, chromium in an amount of 0.027 ppm, cobalt in an amount of 0.001 ppm, copper in an amount of 0.053 ppm, germanium in an amount of 0.081 ppm, iodide in an amount of less than 0.001 ppm, iron in an amount of 0.639 ppm, lead in an amount of 25.908 ppm, magnesium in an amount of 3.753 ppm, manganese in an amount of 0.040 ppm, mercury in an amount of 0.013 ppm, molybdenum in an amount of 0.007 ppm, nickel in an amount of 0.016 ppm, phosphorus in an amount of 3.690 ppm, potassium in an amount of 60.756 ppm, selenium in an amount of 0.202 ppm, silver in an amount of 0.002 ppm, sodium in an amount of 391290 ppm, strontium in an amount of 0.230 ppm, tin in an amount of 0.166 ppm, or zinc in an amount of 0.791 ppm or any combination thereof. In some embodiments, the salt may include one or more of the above elements present in 1, 2, 3, 4, 5, 6, 7, 8, 9, or 10% higher or lower than the above-listed amounts.

In some embodiments, the salt is included in an amount of 0.001, 0.005, 0.01, 0.2, 0.003, 0.04, 0.05, 0.06, 0.07, 0.08, 0.09, 0.1, 0.2, 0.3, 0.4, 0.5, 0.6, 0.7, 0.8, 0.9, 1.0, 1.5, 2.0, 2.5, 3.0, 3.5, 4.0, 4.5, 5, 6, 7, 8, 9, 10, 11, 12, 13, 14, or 15% (w/v), or an amount within a ranged defined by any two of the aforementioned values.

In one embodiment, the salt is sodium chloride (NaCl), lithium chloride (LiCl), hydrogen chloride (HCl), copper chloride ($CuCl_2$), copper sulfate ($CuSO_4$), potassium chloride (KCl), magnesium chloride (MgCl), calcium chloride ($CaCl_2$), or sulfates or phosphates. In some embodiments, the salt can include an additive. Salt additives can include, but are not limited to potassium iodide, sodium iodide, sodium iodate, dextrose, sodium fluoride, sodium ferrocyanide, tricalcium phosphate, calcium carbonate, magnesium carbonate, fatty acids, magnesium oxide, silicon dioxide, calcium silicate, sodium aluminosilicate, calcium aluminosilicate, ferrous fumarate, iron, or folic acid. Any of these additives can be added at this point or at any point during the described process. For example, the above additives can be added just prior to packaging the composition.

In another embodiment, the process can be applied to any ionic, soluble salt mixture, especially with those containing chlorides. In addition to NaCl, other non-limiting examples include LiCl, HCl, $CuCl_2$, $CuSO_4$, KCl, MgCl, $CaCl_2$, sulfates and phosphates. For example, strong acids such as sulfuric acid ($H_2SO_4$), and strong bases such as potassium hydroxide (KOH), and sodium hydroxide (NaOH) are frequently used as electrolytes due to their strong conducting abilities. Preferably the salt is sodium chloride (NaCl). A brine solution can be used to introduce the salt into the water. The amount of brine or salt may be apparent to one of ordinary skill in the art.

Salt can be added to water in the form of a brine solution. To mix the brine solution, a physical mixing apparatus can be used or a circulation or recirculation can be used. In one embodiment, pure pharmaceutical grade sodium chloride is dissolved in the prepared distilled water to form a 15 wt. % sub-saturated brine solution and continuously re-circulated and filtered until the salt has completely dissolved and all particles >0.1 microns are removed. This step can take several days. In one embodiment, the filtered, dissolved brine solution can be injected into tanks of distilled water in about a 1:352 ratio (salt:water) in order to form a 0.3% saline solution. In one embodiment, a ratio 10.75 g of salt per 1 gallon of water can be used to form the composition. In another embodiment, 10.75 g of salt in about 3-4 g of water, such as 3,787.5 g of water can be used to form the composition. This solution then can be allowed to re-circulate and diffuse until homogeneity at the molecular scale has been achieved.

In one embodiment, the homogenous saline solution is chilled to about 4.8±0.5° C. Temperature regulation during the entire electro-catalytic process is typically required as thermal energy generated from the electrolysis process itself may cause heating. In one embodiment, process temperatures at the electrodes can be constantly cooled and maintained at about 4.8° C. throughout electrolysis.

Brine can then be added to the previously treated water or to fresh untreated water to achieve a NaCl concentration of between about 1 g NaCl/gal water and about 25 g NaCl/gal water, between about 8 g NaCl/gal water and about 12 g NaCl/gal water, or between about 4 g NaCl/gal water and about 16 g NaCl/gal water. Once brine is added to water at an appropriate amount, the solution can be thoroughly mixed. The temperature of the liquid during mixing can be at room temperature or controlled to a desired temperature or temperature range.

To mix the solution, a physical mixing apparatus can be used or a circulation or recirculation can be used. The salt solution can be chilled in a chilling step.

For large amounts of composition, various chilling and cooling methods can be employed. For example cryogenic cooling using liquid nitrogen cooling lines can be used. Likewise, the solution can be run through propylene glycol heat exchangers to achieve the desired temperature. The chilling time can vary depending on the amount of liquid, the starting temperature and the desired chilled temperature.

Products from the anodic reactions can be effectively transported to the cathode to provide the reactants to form the stable complexes on the cathode surfaces. Maintaining a high degree of homogeneity in the fluids circulated between the catalytic surfaces can also be helpful. A constant flow of about 2-8 mL/cm$^2$ per sec can be used, with typical mesh electrode distances 2 cm apart in large tanks. This flow can be maintained, in part, by the convective flow of gasses released from the electrodes during electrolysis.

The mixed solution, chilled or not, can then undergo electrochemical processing through the use of at least one electrode in an electrolyzing step. Each electrode can be or include a conductive metal. Metals can include, but are not limited to copper, aluminum, titanium, rhodium, platinum, silver, gold, iron, a combination thereof or an alloy such as steel or brass. The electrode can be coated or plated with a different metal such as, but not limited to aluminum, gold, platinum or silver. In an embodiment, each electrode is formed of titanium and plated with platinum. The platinum surfaces on the electrodes by themselves can be optimal to catalyze the required reactions. Rough, double layered platinum plating can assure that local "reaction centers" (sharply pointed extrusions) are active and that the reactants not make contact with the underlying electrode titanium substrate.

In one embodiment, rough platinum-plated mesh electrodes in a vertical, coaxial, cylindrical geometry can be optimal, with, for example, not more than 2.5 cm, not more than 5 cm, not more than 10 cm, not more than 20 cm, or not more than 50 cm separation between the anode and cathode. The amperage run through each electrode can be between about 2 amps and about 15 amps, between about 4 amps and about 14 amps, at least about 2 amps, at least about 4 amps, at least about 6 amps, or any range created using any of these values. In one embodiment, 7 amps is used with each electrode.

The amperage can be running through the electrodes for a sufficient time to electrolyze the saline solution. The solution can be chilled during the electrochemical process. The solution can also be mixed during the electrochemical process. This mixing can be performed to ensure substantially complete electrolysis.

Electric fields between the electrodes can cause movement of ions. Negative ions can move toward the anode and positive ions toward the cathode. This can enable exchange of reactants and products between the electrodes. In some embodiments, no barriers are needed between the electrodes.

After amperage has been run through the solution for a sufficient time, an electrolyzed solution is created. The solution can be stored and or tested for particular properties in storage/testing step.

The end products of this electrolytic process can react within the saline solution to produce many different chemical entities. The compositions and composition described herein can include one or more of these chemical entities, known as redox signaling agents or RSAs. RSAs can include, but are not limited to superoxides: $O_2^{*-}$, $HO_2^*$; hypochlorites: $OCl^-$, HOCl, NaOCl; hypochlorates: $HClO_2$, $ClO_2$, $HClO_3$, $HClO_4$; oxygen derivatives: $O_2$, $O_3$, $O_4^{*-}$, $^1O$; hydrogen derivatives: $H_2$, $H^-$; hydrogen peroxide: $H_2O_2$; hydroxyl free radical: $OH^{*-}$; ionic compounds: $Na^+$, $Cl^-$, $H^+$, $OH^+$, NaCl, HCl, NaOH; chlorine: $Cl_2$; water clusters: n*$H_2O$-induced dipolar layers around ions, and combinations thereof. Some RSAs are electron acceptors and include HOCl, NaClO, $O_2$, $H_2$, $H^+$, ClO, $Cl_2$, $H_2O_2$ and some are electron donors and include $O_2^-$, $HO_2$, $Cl^-$, $H^-$, *OCl, $O_3$, *$O_2^-$ and $OH^-$.

The chlorine concentration of the electrolyzed solution can be between about 5 ppm and about 34 ppm, between about 10 ppm and about 34 ppm, or between about 15 ppm and about 34 ppm. In one embodiment, the chlorine concentration is about 32 ppm.

The composition generally can include electrolytic and/or catalytic products of pure saline that mimic redox signaling molecular compositions of the native salt water compounds found in and around human cells. The composition can be fine-tuned to mimic or mirror molecular compositions of different biological media. The composition can have reactive species other than chlorine present. As described, species present in the compositions described herein can include, but are not limited to $O_2$, $H_2$, $Cl_2$, $OCl^-$, $HOCl$, $NaOCl$, $HClO_2$, $ClO_2$, $HClO_3$, $HClO_4$, $H_2O_2$, $Na^+$, $Cl^-$, $H^+$, $H^-$, $OH^-$, $O_3$, $O_4^{*-}$, $^1O_2$, $OH^{*-}$, $HOCl-O_2^{*-}$, $HOCl-O_3$, $O_2^{*-}$, $HO_2^*$, $NaCl$, $HCl$, $NaOH$, and water clusters: $n^*H_2O$-induced dipolar layers around ions, and the like.

As used herein, the term "reactive oxygen species (ROS)" refers to chemically reactive molecules containing oxygen. Examples include ozone, peroxides, active chlorines, active oxygens, superoxides, active hydrogens, hydroxyl radical, and singlet oxygen. ROS are formed as a natural byproduct of the normal metabolism of oxygen and have important roles in cell signaling and homeostasis. ROS can include, but are not limited to superoxides ($O_2^{*-}$, $HO_2^*$), hypochlorites ($OCl^-$, $HOCl$, $NaClO$), hypochlorates ($HClO_2$, $ClO_2$, $HClO_3$, $HClO_4$), oxygen derivatives (($O_2$, $O_3$, $O_4^{*-}$, O), hydrogen derivatives ($H_2$, $H^-$), hydrogen peroxide ($H_2O_2$), hydroxyl free radical ($OH^{*-}$), ionic compounds ($Na^+$, $Cl^-$, $H^+$, $OH^-$, $NaCl$, $HCl$, $NaOH$), chlorine ($Cl_2$), water clusters ($n^*H_2O$-induced dipolar layers around ions), and combinations thereof. Some ROS can be electron acceptors and some can be electron donors. In some embodiments, a reactive oxygen species is a hypochlorite.

In some embodiments, the saline solution is electrolyzed to produce an amount of active species, including ozone, active chlorine, active oxygen, or active hydrogen species. In some embodiments, the ozone is present in an amount of 0.1, 0.2, 0.3, 0.4, 0.5, 0.6, 0.7, 0.8, 0.9, 1, 1.5, 2, 2.5, 3, 3.5, 4, 4.5, 5, 6, 7, 8, 9, 10, 15, 20, 25, 30, 35, 40, 45, 50, 60, 70, 80, 90, 100, 150, 200, 250, or 300 ppm or an amount within a range defined by any two of the aforementioned values. In some embodiments, the active chorine species is present in an amount of 0.1, 0.2, 0.3, 0.4, 0.5, 0.6, 0.7, 0.8, 0.9, 1, 1.5, 2, 2.5, 3, 3.5, 4, 4.5, 5, 6, 7, 8, 9, 10, 15, 20, 25, 30, 35, 40, 45, 50, 60, 70, 80, 90, 100, 150, 200, 250, or 300 ppm or an amount within a range defined by any two of the aforementioned values. In some embodiments, the active chorine species is present in an amount of 0.1, 0.2, 0.3, 0.4, 0.5, 0.6, 0.7, 0.8, 0.9, 1, 1.5, 2, 2.5, 3, 3.5, 4, 4.5, 5, 6, 7, 8, 9, 10, 15, 20, 25, 30, 35, 40, 45, 50, 60, 70, 80, 90, 100, 150, 200, 250, or 300 ppm or an amount within a range defined by any two of the aforementioned values. In some embodiments, the active oxygen species is present in an amount of 0.1, 0.2, 0.3, 0.4, 0.5, 0.6, 0.7, 0.8, 0.9, 1, 1.5, 2, 2.5, 3, 3.5, 4, 4.5, 5, 6, 7, 8, 9, 10, 15, 20, 25, 30, 35, 40, 45, 50, 60, 70, 80, 90, 100, 150, 200, 250, or 300 ppm or an amount within a range defined by any two of the aforementioned values. In some embodiments, the active hydrogen species is present in an amount of 0.1, 0.2, 0.3, 0.4, 0.5, 0.6, 0.7, 0.8, 0.9, 1, 1.5, 2, 2.5, 3, 3.5, 4, 4.5, 5, 6, 7, 8, 9, 10, 15, 20, 25, 30, 35, 40, 45, 50, 60, 70, 80, 90, 100, 150, 200, 250, or 300 ppm or an amount within a range defined by any two of the aforementioned values. The process of electrolysis may be performed using any suitable voltage, current, time, or conditions to prepare the saline solution according to the desired concentration of active species.

Pulsing potentials in the power supply of the production units can be built into a system for making the composition. Lack of filter capacitors in the rectified power supply can cause the voltages to drop to zero 120 times per second, resulting in a hard spike when the alternating current in the house power lines changes polarity. This hard spike, under Fourier transform, can emit a large bandwidth of frequencies. In essence, the voltage is varying from high potential to zero 120 times a second. In other embodiments, the voltage can vary from high potential to zero about 1,000 times a second, about 500 times a second, about 200 times a second, about 150 times a second, about 120 times a second, about 100 times a second, about 80 times a second, about 50 times a second, about 40 times a second, about 20 times a second, between about 200 times a second and about 20 times a second, between about 150 times a second and about 100 times a second, at least about 100 times a second, at least about 50 times a second, or at least about 120 times a second. This power modulation can allow the electrodes sample all voltages and also provides enough frequency bandwidth to excite resonances in the forming molecules themselves. The time at very low voltages can also provide an environment of low electric fields where ions of similar charge can come within close proximity to the electrodes. All of these factors together can provide a possibility for the formation of stable complexes capable of generating and preserving ROS free radicals.

Waveforms with an alternating current (AC) ripple can be used to provide power to the electrodes. Such an AC ripple can also be referred to as pulse or spiking waveforms and include: any positive pulsing currents such as pulsed waves, pulse train, square wave, saw tooth wave, pulse-width modulation (PWM), pulse duration modulation (PDM), single phase half wave rectified AC, single phase full wave rectified AC or three phase full wave rectified for example.

A bridge rectifier may be used. Other types of rectifiers can be used such as Single-phase rectifiers, Full-wave rectifiers, Three-phase rectifiers, Twelve-pulse bridge, Voltage-multiplying rectifiers, filter rectifier, a silicon rectifier, an SCR type rectifier, a high-frequency (RF) rectifier, an inverter digital-controller rectifier, vacuum tube diodes, mercury-arc valves, solid-state diodes, silicon-controlled rectifiers and the like. Pulsed waveforms can be made with a transistor regulated power supply, a dropper type power supply, a switching power supply and the like.

This pulsing waveform model can be used to stabilize superoxides, hydroxyl radicals and OOH* from many different components and is not limited to any particular variable such as voltage, amps, frequency, flux (current density) or current. The variables are specific to the components used. For example, water and NaCl can be combined which provide molecules and ions in solution. A 60 Hz current can be used, meaning that there are 60 cycles/120 spikes in the voltage (V) per second or 120 times wherein the V is 0 each second. When the V goes down to 0 it is believe that the 0 V allows for ions to drift apart/migrate and reorganize before the next increase in V. Without wishing to be bound by theory, the spiking in V allows for and promotes a variable range of frequencies influencing many different types of compounds and/or ions.

Diodes may also be used. The V may drop to 0 as many times per second as the frequency is adjusted. As the frequency is increased the number of times the V drops is increased.

When the ions are affected by the electricity from the electrodes, they change. While still not wishing to be bound by theory, it is believed that the electricity alters the state of some of the ions/compounds. This alteration results in the pushing of electrons out of their original orbit and/or spin state into a higher energy state and/or a single spin state. This electrolysis provides the energy to form free radicals which are ultimately formed during a multi-generational cycling of reactants and products during the electrolysis process. In other words, compounds and/or ions are initially electrolyzed so that the products that are formed are then themselves reacted with other compounds and/or ions and/or gas to form a second generation of reactants and products. This generational process then happens again so that the products from the second generation react with other compounds and/or ions in solution when the voltage spikes again.

In some embodiments, the redox potential can be about 840 mV. In some embodiments, the frequency can be from about 1 Hz to infinity or to about 100 MHz In some embodiments, end products of the electrolytic process can react within the saline solution to produce different chemical entities. The compositions described herein can include one or more of these chemical entities. These end products can include, but are not limited to superoxides: $O_2^{*-}$, $HO_2^*$; hypochlorites: $OCl^-$, $HOCl$, $NaOCl$; hypochlorates: $HClO_2$, $ClO_2$, $HClO_3$, $HClO_4$; oxygen derivatives: $O_2$, $O_3$, $O_4^{*-}$, $^1O$; hydrogen derivatives: $H_2$, $H^-$; hydrogen peroxide: $H_2O_2$; hydroxyl free Radical: $OH^{*-}$; ionic compounds: $Na^+$, $Cl^-$, $H^+$, $OH^-$, $NaCl$, $HCl$, $NaOH$; chlorine: $Cl_2$; and water clusters: $n*H_2O$-induced dipolar layers around ions, several variations.

In order to determine the relative concentrations and rates of production of each of these during electrolysis, certain general chemical principles can be helpful:

1) A certain amount of Gibbs free energy is required for construction of the molecules; Gibbs free energy is proportional to the differences in electrode potentials. Reactions with large energy requirements are less likely to happen, for example an electrode potential of −2.71 V (compared to hydrogen reduction at 0.00 V) is required to make sodium metal: $Na^+ + e^- \rightarrow Na(s)$.

Such a large energy difference requirement makes this reaction less likely to happen compared to other reactions with smaller energy requirements. Electron(s) from the electrodes may be preferentially used in the reactions that require lesser amounts of energy, such as the production of hydrogen gas.

2) Electrons and reactants are required to be at the same micro-locality on the electrodes. Reactions that require several reactants may be less likely to happen, for example: $Cl_2 + 6 H_2O \rightarrow 10 e^- + 2 ClO_3^- + 12 H^+$.

This reaction requires six water molecules and one $Cl_2$ molecule to be at the electrode at the same point at the same time and a release of 10 electrons to simultaneously occur. The probability of this happening generally is smaller than other reactions requiring fewer and more concentrated reactants to coincide, but such a reaction may still occur.

3) Reactants generated in preceding generations can be transported or diffuse to the electrode where reactions happen. For example, dissolved oxygen ($O_2$) produced on the anode from the first generation can be transported to the cathode in order to produce superoxides and hydrogen peroxide in the second generation. Ions can be more readily transported: they can be pulled along by the electric field due to their electric charge. In order for chlorates, to be generated, for example, $HClO_2$ can first be produced to start the cascade, restrictions for $HClO_2$ production can also restrict any subsequent chlorate production. Lower temperatures can prevent $HClO_2$ production.

Stability and concentration of the above products can depend, in some cases substantially, on the surrounding environment. The formation of complexes and water clusters can affect the lifetime of the moieties, especially the free radicals.

In a pH-neutral aqueous solution (pH around 7.0) at room temperature, superoxide free radicals ($O_2^{*-}$) have a half-life of 10's of milliseconds and dissolved ozone ($O_3$) has a half-life of about 20 minutes. Hydrogen peroxide ($H_2O_2$) is relatively long-lived in neutral aqueous environments, but this can depend on redox potentials and UV light. Other entities such as $HCl$ and $NaOH$ rely on acidic or basic environments, respectively, in order to survive. In pH-neutral solutions, $H^+$ and $OH^-$ ions have concentrations of approximately 1 part in 10,000,000 in the bulk aqueous solution away from the electrodes. $H^-$ and $^1O$ can react quickly. The stability of most of these moieties mentioned above can depend on their microenvironment.

Superoxides and ozone can form stable van der Waals molecular complexes with hypochlorites. Clustering of polarized water clusters around charged ions can also have the effect of preserving hypochlorite-superoxide and hypochlorite-ozone complexes. Such complexes can be built through electrolysis on the molecular level on catalytic substrates, and may not occur spontaneously by mixing together components. Hypochlorites can also be produced spontaneously by the reaction of dissolved chlorine gas ($Cl_2$) and water. As such, in a neutral saline solution the formation of one or more of the stable molecules and complexes may exist: dissolved gases: $O_2$, $H_2$, $Cl_2$; hypochlorites: $OCl^-$, $HOCl$, $NaOCl$; hypochlorates: $HClO_2$, $ClO_2$, $HClO_3$, $HClO_4$; hydrogen peroxide: $H_2O_2$; ions: $Na^+$, $Cl^-$, $H^+$, $H^-$, $OH^-$; ozone: $O_3$, $O_4^{*-}$; singlet oxygen: $^1O$; hydroxyl free radical: $OH^{*-}$; superoxide complexes: $HOCl-O_2^{*-}$; and ozone complexes: $HOCl-O_3$. One or more of the above molecules can be found within the compositions described herein.

A complete quantum chemical theory can be helpful because production is complicated by the fact that different temperatures, electrode geometries, flows and ion transport mechanisms and electrical current modulations can materially change the relative/absolute concentrations of these components, which could result in producing different distinct compositions. As such, the selection of production parameters can be critical. The amount of time it would take to check all the variations experimentally may be prohibitive.

The chlorine concentration of the electrolyzed solution can be about 5 ppm, about 10 ppm, about 15 ppm, about 20 ppm, about 21 ppm, about 22 ppm, about 23 ppm, about 24 ppm, about 25 ppm, about 26 ppm, about 27 ppm, about 28 ppm, about 29 ppm, about 30 ppm, about 31 ppm, about 32 ppm, about 33 ppm, about 34 ppm, about 35 ppm, about 36 ppm, about 37 ppm, about 38 ppm, less than about 38 ppm, less than about 35 ppm, less than about 32 ppm, less than about 28 ppm, less than about 24 ppm, less than about 20 ppm, less than about 16 ppm, less than about 12 ppm, less than about 5 ppm, between about 30 ppm and about 34 ppm, between about 28 ppm and about 36 ppm, between about 26 ppm and about 38 ppm, between about 20 ppm and about 38 ppm, between about 5 ppm and about 34 ppm, between about 10 ppm and about 34 ppm, or between about 15 ppm and about 34 ppm. In one embodiment, the chlorine concentration is about 32 ppm. In another embodiment, the chlorine concentration is less than about 41 ppm.

The saline concentration in the electrolyzed solution can be about 0.10% w/v, about 0.11% w/v, about 0.12% w/v, about 0.13% w/v, about 0.14% w/v, about 0.15% w/v, about 0.16% w/v, about 0.17% w/v, about 0.18% w/v, about 0.19% w/v, about 0.20% w/v, about 0.30% w/v, about 0.40% w/v, about 0.50% w/v, about 0.60% w/v, about 0.70% w/v, between about 0.10% w/v and about 0.20% w/v, between about 0.11% w/v and about 0.19% w/v, between about 0.12% w/v and about 0.18% w/v, between about 0.13% w/v and about 0.17% w/v, or between about 0.14% w/v and about 0.16% w/v.

The composition generally can include electrolytic and/or catalytic products of pure saline that mimic redox signaling molecular compositions of the native salt water compounds found in and around human cells. The composition can be fine-tuned to mimic or minor molecular compositions of different biological media. The composition can have reactive species other than chlorine present. As described, species present in the compositions described herein can include, but are not limited to $O_2$, $H_2$, $Cl_2$, $OCl^-$, $HOCl$, $NaOCl$, $HClO_2$, $ClO_2$, $HClO_3$, $HClO_4$, $H_2O_2$, $Na^+$, $Cl^-$, $H^+$, $H^-$, $OH^-$, $O_3$, $O_4^{*-}$, $^1O$, $OH^{*-}$, $HOCl\text{—}O_2^{*-}$, $HOCl\text{—}O_3$, $O_2^*$, $HO_2^*$, $NaCl$, $HCl$, $NaOH$, and water clusters: $n^*H_2O$- induced dipolar layers around ions, several variations.

In some embodiments, hydroxyl radicals can be stabilized in the composition by the formation of radical complexes. The radical complexes can be held together by hydrogen bonding. Another radical that can be present in the composition is an $OOH^*$ radical. Still other radical complexes can include a nitroxyl-peroxide radical ($HNO\text{—}HOO^*$) and/or a hypochlorite-peroxide radical ($HOCl\text{—}HOO^*$).

Concentrations of reactive species in the electrolyzed saline solutions, detected by fluorescence photo spectroscopy, may not significantly decrease in time. Mathematical models show that bound $HOCl\text{—}^*O_2^-$ complexes are possible at room temperature. Molecular complexes can preserve volatile components of reactive species. For example, reactive species concentrations in whole blood as a result of molecular complexes may prevent reactive species degradation over time.

Reactive species can be further divided into "reduced species" (RS) and "reactive oxygen species" (ROS). Reactive species can be formed from water molecules and sodium chloride ions when restructured through a process of forced electron donation. Electrons from lower molecular energy configurations in the salinated water may be forced into higher, more reactive molecular configurations. The species from which the electron was taken can be "electron hungry" and is called the RS and can readily become an electron acceptor (or proton donor) under the right conditions. The species that obtains the high-energy electron can be an electron donor and is called the ROS and may energetically release these electrons under the right conditions.

In some embodiments, the composition can include sodium present at a concentration of 100 to 2500 ppm, including about 100, 200, 300, 400, 500, 600, 700, 800, 900, 1000, 1100, 1200, 1300, 1400, 1500, 1600, 1700, 1800, 1900, 2000, 2100, 2200, 2300, 2400, or 2500 ppm, or an amount within a range defined by any two of the aforementioned values, with the sodium measured by methods known in the art, including, for example, inductively coupled plasma mass spectrometry (ICP-MS). In yet other embodiments, the composition can include chloride present at a concentration of 0 to 2500 ppm, including about 0, 0.5, 1, 5, 10, 25, 50, 100, 200, 300, 400, 500, 600, 700, 800, 900, 1000, 1100, 1200, 1300, 1400, 1500, 1600, 1700, 1800, 1900, 2000, 2100, 2200, 2300, 2400, or 2500 ppm, or an amount within a range defined by any two of the aforementioned values, with the chloride measured by methods known in the art, including, for example, inductively coupled plasma mass spectrometry (ICP-MS) or $^{35}Cl$ nuclear magnetic resonance ($^{35}Cl$ NMR). In other embodiments, the composition can include hypochlorite or an acid or salt thereof present at a concentration of about 10 to about 3000 ppm, including about 10, 11, 12, 13, 14, 15, 16, 17, 18, 19, 20, 21, 22, 23, 24, 25, 26, 27, 28, 29, 30, 40, 50, 60, 70, 80, 90, 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, or 3000 ppm, or an amount within a range defined by any two of the aforementioned values, with the hypochlorite or an acid or salt thereof measured by methods known in the art, including, for example, colorimetry or $^{35}Cl$ nuclear magnetic resonance ($^{35}Cl$ NMR). In some embodiments, the composition can include superoxide radical present at a concentration of 10 to 200 μM, including about 10, 20, 30, 40, 50, 60, 70, 75, 80, 85, 90, 91, 92, 93, 94, 95, 96, 97, 98, 99, 100, 110, 120, 130, 140, 150, 160, 170, 180, 190, or 200 μM or an amount within a range defined by any two of the aforementioned values, with the superoxide radical measured by methods known in the art, including, for example, 5-(diisopropoxyphosphoryl)-5-1-pyrroline-N-oxide nuclear magnetic resonance (DIPPMPO-NMR). In other embodiments, the composition can include hydroxyl radical present at a concentration of 0 to 300 μM, including about 0, 1, 2, 3, 4, 5, 6, 7, 8, 9, 10, 20, 30, 40, 50, 60, 70, 80, 90, 100, 110, 120, 130, 140, 150, 160, 170, 180, 190, 200, 210, 220, 225, 230, 235, 240, 241, 242, 243, 244, 245, 250, 255, 260, 270, 280, 290, or 300 μM or an amount within a range defined by any two of the aforementioned values, with the hydroxyl radical measured by methods known in the art, including, for example, DIPPMPO-NMR or mass spectrometry (MS). In yet other embodiments, the composition can include no hydroxyl radical.

In yet other embodiments, the composition can have a pH between about 5 and about 9, such as a pH of 5, 5.5, 6, 6.5, 7, 7.1, 7.2, 7.3, 7.4, 7.5, 7.6, 7.7, 7.8, 7.9, 8, 8.5, or 9 or a pH within a range defined by any two of the aforementioned values. In some embodiments, the sodium, chloride, hypochlorite or an acid or salt thereof, superoxide radical, and hydroxyl radical can be measured less than one year after the composition was made. In some embodiments, the formulation can be administered to a user orally.

In some embodiments, the electrolyzed solution including hypochlorite is formulated in a dosage formulation for nasal, oral, parenteral, pulmonary, rectal, sublingual, topical, or vaginal administration.

The composition can be packaged in a packaging step. The packaging will depend on the formulation of the composition, whether formulated for nasal, oral, parenteral, pulmonary, rectal, sublingual, topical, or vaginal administration. Thus, in some embodiments, the composition is formulated as a solution, a spray, a mist, an aerosol, a powder, a nasal inhalable, a pill, a tablet, a capsule, a caplet, a lozenge, a gummy, a soft gel, a bead, a pellet, a strip, a dragee, a granule, a slurry, a foam, a drop, a liquid, a suspension, a syrup, an oral inhalable, an injectable, a suppository, a drop, a paste, a lotion, a gel, a cream, a spritz, an ointment, an emollient, a balm, a patch, a meltable solid, a sponge, a tape, or a vapor. The type of formulation dictates the type of packaging.

Packaging materials used herein can aid in preventing decay of free radical species found within the composition. In other embodiments, the bottles and pouches described do not further the decay process. In some embodiments, the packaging used can be inert with respect to the radical species in the composition. In one embodiment, a container (for example, bottle and/or pouch) can allow less than about 10% decay/month, less than about 9% decay/month, less than about 8% decay/month, less than about 7% decay/month, less than about 6% decay/month, less than about 5% decay/month, less than about 4% decay/month, less than about 3% decay/month, less than about 2% decay/month, less than about 1% decay/month, between about 10% decay/month and about 1% decay/month, between about 5% decay/month and about 1% decay/month, about 10% decay/month, about 9% decay/month, about 8% decay/month, about 7% decay/month, about 6% decay/month, about 5% decay/month, about 4% decay/month, about 3% decay/month, about 2% decay/month, or about 1% decay/month of free radicals in the composition.

The composition may be presented in a pack or dispenser device, which may contain one or more unit dosage forms containing the composition. The pack may be specific to the mode of administration, and may for example include metal or plastic foil, such as a blister pack, or a single or serial injectable packaging. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. The composition comprising hypochlorite may be placed in an appropriate container, and labeled for treatment or inhibition of an indicated condition, such as for treatment or inhibition of a TBI, such as a concussion.

The compositions described herein may further include an additive known in the art. In some embodiments, the additive includes a compound that improves the formulation for the mode of administration. In some embodiments, the additive improves the efficacy of the composition. In some embodiments, the additive improves the shelf life of the composition. In some embodiments, the additive is included for aesthetic purposes to improve the appearance, texture, scent, or feel of the composition. Exemplary additives for including in a composition can include moisturizers, humectants, pigments, dyes, pearlescent compounds, nacreous pigments, bismuth oxychloride coated mica, titanium dioxide coated mica, colorants, fragrances, biocides, preservatives, lipolytic agent, diuretics, xanthines (such as caffeine, theophylline, and aminophylline), alpha hydroxy acids, antioxidants, lymphatic drainage agent, antiperspirant agents, exfoliants, hormones, anticellulitic, enzymes, medicinal compounds, vitamins, minerals, electrolytes, alcohols, polyols, polypropylene glycol, anti-adipogenesis agents, retinoids, retinol, polyisobutene, polyoxyethylene, behenic acid, behenyl, sugar-alcohols, absorbing agents for ultraviolet radiation, botanical extracts, surfactants, silicone oils, organic oils, waxes, alkaline or acidic or buffering agents, film formers, thickening agents, hyaluronic acid, fumed silica, hydrated silica, talc, kaolin, starch, modified starch, mica, nylon, clay, bentonite, organo-modified clays, and combinations thereof.

The disclosure is generally described herein using affirmative language to describe the numerous embodiments. The disclosure also includes embodiments in which subject matter is excluded, in full or in part, such as substances or materials, method steps and conditions, protocols, or procedures.

EXAMPLES

Additional alternatives are disclosed in further detail in the following examples, which are not in any way intended to limit the scope of the claims.

Example 1

Method of Making a Composition Including Hypochlorite

The following example describes an embodiment for preparing a composition including hypochlorite in an oral liquid formulation.

One skilled in the art understands that changes can be made to the system to alter the composition, and these changes are within the scope of the present description. Incoming water was subjected to reverse osmosis system at a temperature of about 15-20° C. to achieve purified water with about 8 ppm of total dissolved solids. Purified water was fed at a temperature of about 15-20° C. into distiller and processed to achieve distilled water with about 0.5 ppm of total dissolved solids. Distilled water was stored in a storage tank.

The distilled water was further processing into a composition. A water source fed directly into a carbon filter to remove oils, alcohols, and other volatile chemical residuals and particulates. The water was directed to resin beds within a water softener to remove dissolved minerals. The water passed through reverse osmosis system and distiller.

Distilled water was gravity fed as needed from the storage tank into a saline storage tank cluster using a feed line. The saline storage tank cluster included 12 tanks. Each tank was filled to about 1,300 gallons with distilled water. A handheld meter was used to test distilled water for salinity.

The saline storage tank cluster was salted using a brine system. The brine system included two brine tanks having a capacity of about 500 gallons. Brine tanks were filled to 475 gallons with distilled water and sea salt was added to the brine tanks at a ratio of about 537.5 g/gal of liquid. The water circulated in the brine tanks at a rate of about 2,000 gal/hr. for about 4 days.

Prior to addition of brine, the salinity of the water in tanks was tested using a handheld conductivity meter such as an YSI ECOSENSE® ecp300 (YSI Inc., Yellow Springs, Ohio). Any corrections based on the salinity measurements were made at this point. Brine solution was added to the tanks to achieve a salt concentration of about 10.75 g/gal. The salted water was circulated in the tanks at a rate of about 2,000 gal/hr. for no less than about 72 hours. This circulation was performed at room temperature. A handheld probe was used to test salinity of the salinated solution.

Salinated water was transferred to cold saline tanks. The amount of salinated water was about 1,000 gal. A chiller such as a 16 ton chiller was used to cool heat exchangers to about 0-5° C. The salinated water was circulated through the heat exchangers which were circulated with propylene glycol until the temperature of the salinated water was about 4.5-5.8° C. Chilling the 1,000 gal of salinated water generally takes about 6-8 hr.

Cold salinated water was transferred to processing tanks. Each processing tank was filled to about 125 gal for a total of 1,000 gal. Heat exchangers were used to chill the cold salinated water added to processing tanks. Each processing tank included a cylinder of chilling tubes and propylene glycol was circulated. The heat exchangers were powered by a 4-5 ton chiller. The temperature of cold salinated water was 4.5-5.8° C. during processing.

Prior to transferring aged salt water to processing tanks, the aged salt water was agitated for about 30 minutes to sufficiently mix the aged salt water. The recirculation valves were closed, and the appropriate inlet valve on the production tank was opened, and the tank filled so that the salt water covered the cooling coils (approximately 125 gallons).

Once the aged salt water reached production temperature, the pump was turned off but the chiller left on. The tank was adequately agitated or re-circulated during the whole duration of electrochemical processing and the temperature remained constant throughout.

Each processing tank included an electrode. Electrodes were 3 inches tall circular structures formed of titanium and plated with platinum. Electrochemical processing of the cold salinated water lasted about 8 hours. A power supply was used to power the eight electrodes (one in each processing tank) to 7 amps each for a total of 56 amps. The cold salinated water was circulated during electrochemical processing at a rate of about 1,000 gal/hr.

An independent current meter was used to set the current to around 7.0 Amps. Attention was paid to ensure that the voltage did not exceed 12V and did not go lower than 9V. Normal operation was about 10V. Alternatively, normal operation can be at 1V, 2V, 3V, 4V, 5V, 6V, 7V, 8V, 9V, 10V, 11V or 12V.

A run timer was set for a prescribed time (about 4.5 to 5 hours). Each production tank included its own timer and/or power supply. Electrodes were turned off after the timer expired.

The production tanks were checked periodically. The temperature and/or electrical current was kept substantially constant. At the beginning, the electrodes were visible from the top, emitting visible bubbles. After about 3 hours, small bubbles of un-dissolved oxygen began building up in the tank as oxygen saturation occurred, obscuring the view of the electrodes. A slight chlorine smell was detected.

After the 8 hour electrochemical processing was complete, a composition with hypochlorite in an amount of about 75 ppm was generated. The composition was transferred to storage tanks.

Example 2

Compositions for Treating a Concussion

The following example describes an embodiment showing alleviation, amelioration, palliation, reduction, or treatment of a concussion in subjects that are administered a composition including hypochlorite.

The composition described in Example 1 is formulated as a liquid for oral administration to a subject. The composition includes hypochlorite in an amount of about 75 ppm.

Participants are selected who suffered from or are suspected of suffering from a concussion. The participants are randomized into test (group A), placebo (group B), or control group (group C). Test group are administered the liquid composition in an amount of four ounces daily. Placebo receives water and control group receives no composition. Participants complete a health questionnaire and a symptoms log over the course of the study. Symptoms of concussion are monitored over an 8-week period to detect changes in symptoms in the test group as compared to placebo and control groups.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method of treating a traumatic brain injury (TBI) in a subject, comprising:
    administering to the subject a composition comprising hypochlorite, a salt present in an amount of about 0.01% to about 0.1% w/v, a buffer present in an amount of about 0.5% to about 5% w/v, wherein the buffer comprises sodium phosphate monobasic, a rheology agent present in an amount of about 0.5% to about 10% w/v, wherein the rheology agent comprises sodium magnesium silicate, and a silicone polymer or blend thereof present in an amount of about 0.5% to about 10% w/v, wherein the silicone polymer or blend thereof comprises dimethicone,
    wherein the composition is administered by nasal, oral, parenteral, pulmonary, rectal, sublingual, or vaginal administration.

2. The method of claim 1, wherein the salt comprises halite, table salt, common salt, curing salt, flake salt, Epsom salt, sea salt, Alaea salt (or Hawaiian sea salt), Alpenbergkern salt, Anglesey Sea salt, Dead Sea salt, Himalayan sea salt, Kalahari salt, Maras salt, Namibian salt pearls, Persian blue fine salt, Polish mine salt, primordial sea salts, Sal de Tavira, Sale Marino di Trapani, Sel de Guérande, South African Sea salt, Utah salt, black lava salt, brine, rock salt, red rock salt, or kosher salt, or combinations thereof.

3. The method of claim 1, wherein the composition is formulated as a pharmaceutically acceptable dosage form.

4. The method of claim 1, wherein the TBI is a concussion.

5. The method of claim 1, wherein the composition is formulated as an aerosol, a balm, a bead, a caplet, a capsule, a cream, a dragee, a drop, an emollient, a foam, a gel, a granule, a gummy, an inhalable, an injectable, a liquid, a lotion, a lozenge, a meltable solid, a mist, an ointment, a paste, a patch, a pellet, a pill, a powder, a slurry, a soft gel, a solution, a sponge, a spray, a spritz, a strip, a suppository, a suspension, a syrup, a tablet, a tape, or a vapor.

6. The method of claim 1, wherein the composition is administered to the subject at least twice daily.

7. The method of claim 1, wherein administration of the composition reduces symptoms of a TBI.

8. The method of claim 1, wherein the composition is administered by nasal administration.

9. The method of claim 1, wherein the composition is administered by oral administration.

10. The method of claim 1, wherein the composition is administered by parenteral administration.

11. The method of claim 1, wherein the composition is administered by pulmonary administration.

12. The method of claim 1, wherein the composition is administered by rectal administration.

13. The method of claim 1, wherein the composition is administered by sublingual administration.

14. The method of claim 1, wherein the composition is administered by vaginal administration.

15. The method of claim 1, wherein the composition is administered in an amount of about 0.1 ounces to about 12 ounces.

16. The method of claim 1, wherein the TBI is a chronic brain injury.

17. The method of claim 1, wherein the hypochlorite is present in an amount of about 10 ppm to about 300 ppm.

18. The method of claim 1, wherein the hypochlorite is present in an amount of about 75 ppm.

* * * * *